United States Patent [19]

Burton et al.

[11] Patent Number: 5,602,117
[45] Date of Patent: Feb. 11, 1997

[54] CEPHALOSPORIN COMPOUNDS

[75] Inventors: George Burton, Wallington; Stephen C. M. Fell, Horsham, both of England

[73] Assignee: Pfizer Inc., New York, N.Y.

[21] Appl. No.: 244,568

[22] PCT Filed: Dec. 1, 1992

[86] PCT No.: PCT/GB92/02231

§ 371 Date: Jun. 1, 1994

§ 102(e) Date: Jun. 1, 1994

[87] PCT Pub. No.: WO93/11131

PCT Pub. Date: Jun. 10, 1993

[30] Foreign Application Priority Data

Dec. 3, 1991 [GB] United Kingdom ............... 9125645

[51] Int. Cl.$^6$ .................................................. A61K 31/545
[52] U.S. Cl. .......................... 514/202; 514/201; 540/221; 540/222; 540/301
[58] Field of Search ................................. 540/222, 227, 540/221; 514/202

[56] References Cited

U.S. PATENT DOCUMENTS 5,036,034  7/1991  Gotschi .................................. 540/227
5,276,024  1/1994  Schneider et al. ..................... 540/226

FOREIGN PATENT DOCUMENTS 0392796  10/1990  European Pat. Off. .
0395219  10/1990  European Pat. Off. .
92/01696  2/1992  WIPO .
92/04353  3/1992  WIPO .

OTHER PUBLICATIONS

Conant, The Chemistry of Organic Compounds pp. 269, 520–523 (1934).

Primary Examiner—Mukund J. Shah
Assistant Examiner—Pavanaram K. Sripada
Attorney, Agent, or Firm—Peter C. Richardson; Paul H. Ginsburg; Lorraine B. Ling

[57] ABSTRACT

β-lactam antibiotics of formula (I) or a salt thereof, wherein $R^1$ is hydrogen, methoxy of formamido; $R^2$ is an acyl group, in particular that of an antibacterially active cephalosporin; $CO_2R^3$ is a carboxy group or a carboxylate anion, or $R^3$ is a readily removable carboxy protecting group (such as a pharmaceutically acceptable in vivo hydrolysable ester group); $R^4$ represents up to four substituents selected from alkyl, alkenyl, alkynyl, alkoxy, hydroxy, halogen, amino, alkylamino, acylamino, dialkylamino, $CO_2R$, $CONR_2$, $SO_2NR_2$ (where R is hydrogen or $C_{1-6}$ alkyl), aryl and heterocyclyl, which may be the same or different and wherein any $R^4$ alkyl substituent is optionally substituted by any other $R^4$ substituent; X is S, SO, $SO_2$, O or $CH_2$; Y is S, SO or $SO_2$; and m is 1 or 2, useful in the treatment of bacterial infections in humans and animals.

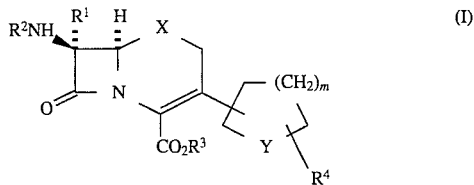

9 Claims, No Drawings

CEPHALOSPORIN COMPOUNDS

This application is a 371 of PCT/GB 92/02231 filed Dec. 01, 1992.

This invention relates to novel β-lactam containing compounds, their preparation and their use, and in particular to a novel class of cephalosporins. These compounds have antibacterial properties, and are therefore of use in the treatment of bacterial infections in humans and animals caused by a wide range of organisms.

We have found a particular class of cephalosporins bearing a cyclic thio-ether substituent at the 3-position of the cephalosporin nucleus that possesses prolonged and high levels of antibacterial activity, and shows good absorption both parentally and orally, especially orally.

The present invention provides a compound of formula (I) or a salt thereof:

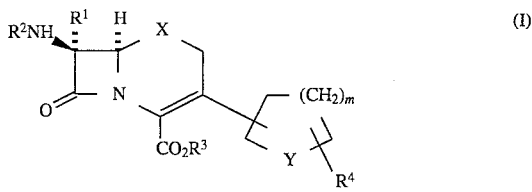

wherein
$R^1$ is hydrogen, methoxy or formamido;
$R^2$ is an acyl group, in particular that of an antibacterially active cephalosporin;
$CO_2R^3$ is a carboxy group or a carboxylate anion, or $R^3$ is a readily removable carboxy protecting group (such as a pharmaceutically acceptable in vivo hydrolysable ester group); $R^4$ represents hydrogen or up to four substituents selected from alkyl, alkenyl, alkynyl, alkoxy, hydroxy, halogen, amino, alkylamino, acylamino, dialkyimino, $CO_2R$, $CONR_2$, $SO_2NR_2$ (where R is hydrogen or $C_{1-6}$ alkyl), aryl and heterocyclyl, which may be the same or different and wherein any $R^4$alkyl substituent is optionally substituted by any other $R^4$ substituent; X is $S, SO, SO_2, O$ or $CH_2$; Y is S, SO or $SO_2$; and m is 1 or 2.

The bonding carbon atom of the cyclic thio-ether moiety which links the ring to the cephalosporin nucleus is generally asymmetric. The present includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

Since the β-lactam antibiotic compounds of the present invention are intended for use as therapeutic agents in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

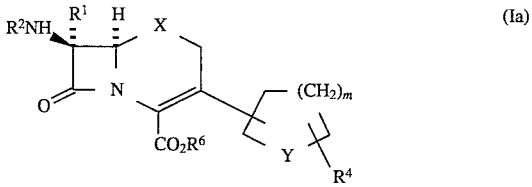

wherein $R^1$, $R^2$, $R^4$, m and X are as defined with respect to formula (I) and the group $CO_2R^6$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective amount of an antibiotic compound of this invention of the formula (Ia) or a pharmaceutically acceptable in vivo hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus- containing group, an oxime radical of formula —N=CHR$^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $C_{1-6}$ alkyl, phenyl, $C_{1-6}$ alkoxy, hydroxy($C_{1-6}$)alkyl, mercapto($C_{1-6}$)alkyl, halo($C_{1-6}$) alkyl, hydroxy, amino, nitro, carboxy, $C_{1-6}$ alkylcarbonyloxy, alkoxycarbonyl, formyl, or $C_{1-6}$ alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo$(C_{1-6})$alkyl, hydroxy, carboxy, carboxy salts, carboxy esters such as $(C_{1-6})$alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein the terms 'alkyl' alkenyl, alkynyl and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriate to the particular $R^3$ group, for example, acid- and base- catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

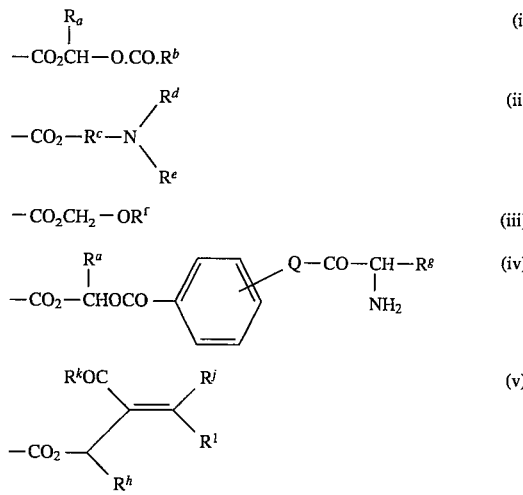

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{3-7}$ cycloalkyloxy, $C_{1-6}$ alkyl $C_{3-7}$ cycloalkyl, 1-amino $C_{1-6}$ alkyl, or 1-$(C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; Q is oxygen or NH; $R^h$ is hydrogen or $C_{1-6}$ alkyl; $R^i$ is hydrogen, $C_{1-6}$ alkyl optionally substituted by halogen, $C_{2-6}$ alkenyl, $C_{1-6}$ alkoxycarbonyl, aryl or heteroaryl; or $R^h$ and $R^i$ together form $C_{1-6}$ alkylene; $R^j$ represents hydrogen, $C_{1-6}$ alkyl or $C_{1-6}$ alkoxycarbonyl; and $R^k$ represents $C_{1-8}$ alkyl, $C_{1-8}$ alkoxy, $C_{1-6}$ alkoxy$(C_{1-6})$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl)but-2-enyl; lactone groups such as phthalidyl and dimethoxyphthalidyl; and esters linked to a second β-lactam antibiotic or to a β-lactamase inhibitor.

A preferred in vivo hydrolysable ester group is the pivaloyloxymethyl ester.

A further suitable pharmaceutically acceptable in vivo hydrolysable ester group is that of the formula:

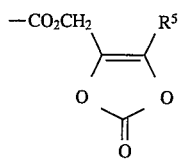

wherein $R^5$ is hydrogen, $C_{1-6}$ alkyl or phenyl.

Suitable pharmaceutically acceptable salts of the carboxy group of the compound of formula (I) include metal salts, e.g. aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)- amine, cycloalkylamines such as dicyclohexylamine, or with procaine, dibenzylamine, N,N-dibenzylethylene- diamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (I) or (Ia), the group X may be sulphur or an oxidised sulphur atom, i.e. a sulphoxide (SO) or sulphone (SO$_2$) group. When X is a sulphoxide group it will be understood that α- and β-isomers may exist; both such isomers are encompassed within the scope of the present invention.

Examples of X include S, SO, SO$_2$, O and CH$_2$. Preferably X is sulphur or CH$_2$.

In compounds of formula (I) or (Ia), the group Y may be sulphur or an oxidised sulphur atom, i.e. a sulphoxide (SO) or sulphone (SO$_2$) group. When Y is a sulphoxide group it will be understood that α- and β-isomers may exist; both such isomers are encompassed within the scope of the present invention.

Advantageously, $R^1$ is hydrogen.

Suitably, the cyclic thio-ether at the 3-position of the cephalosporin nucleus is unsubstituted or substituted by up to three substituents, $R^4$, selected from $C_{1-6}$ alkyl, for example methyl, $C_{1-6}$ alkoxy, for example methoxy, $C_{1-6}$ alkoxycarbonyl for example methoxycarbonyl, $C_{1-6}$ alkoxy $C_{1-6}$ alkyl, for example methoxymethyl, and $C_{1-6}$ alkanoyloxy $C_{1-6}$ alkyl, for example acetoxymethyl. Preferably the cyclic thio-ether at the 3-position of the cephalosporin nucleus is unsubstituted.

Preferably m is 1.

Preferably the cyclic thio-ether is bonded to the cephalosporin nucleus at a ring carbon adjacent to the sulphur heteroatom.

Suitable acyl groups $R^2$ include those of formulae (a)-(f):

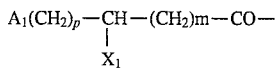  (a)

$A_2CO—$  (b)

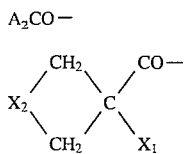  (c)

$A_2—X_3—(CH_2)_p—CO—$  (d)

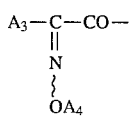  (e)

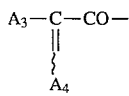  (f)

wherein p is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic (including heteroaromatic) group, such as phenyl, substituted phenyl, thienyl, pyridyl, or an optionally substituted thiazolyl group, a $C_{1-6}$ akylthio group or $C_{1-6}$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a $—CH_2OCH_2—$, $—CH_2SCH_2—$ or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $C_{1-6}$alkyl, $C_{3-8}$ cycloalkyl, $C_{3-8}$ cycloalkyl($C_{1-6}$)alkyl, $C_{1-6}$ alkoxycarbonyl($C_{1-6}$) alkyl, $C_{2-6}$ alkenyl, carboxy($C_{1-6}$)alkyl, $C_{2-6}$ alkynyl, aryl or $C_{1-6}$alkyl substituted by up to three aryl groups.

The term 'heteroaryl' as used herein means a heteroaromatic heterocyclic ring or ring system, suitably having 5 or 6 ring atoms in each ring.

Suitably when $R^2$ is a group (a), $A_1$ is $C_{1-6}$ alkyl, $C_{3-6}$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is O.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl, pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-_amino-1,2,4-thiadiazol-3-yl and 4-aminopyrimid-2-yl.

In compounds of formula (Ia), a particularly preferred group for $A_3$ is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the sin configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Certain compounds of the invention include an amino group which may be protected. Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following pharmaceutically acceptable carboxylic adds, salts and in-vivo hydrolysable esters:

sodium (6R,7R)-7-[2-(2-aminothiazol-4-yl)-2-(Z)-methoxyiminoacetamido]-3-[(RS)-tetrahydrothien-2-yl]-ceph-3-em-4-carboxylate;

pivaloyloxymethyl (6R,7R)-7-[2-(2-aminothiazol-4-yl)-2-(Z)-methoxyiminoacetamido]-3-[(RS)-tetrahydrothien-2yl-]ceph-3-em-4-carboxylate; and sodium (6R,7R)-7-[2-(2-aminothiazol-4-yl)-2-(Z)-methoxyiminoacetamido]-3-[1,1-dioxotetrahydrothien-2-yl]-ceph-3-em-4-carboxylate The present invention further provides a process for the preparation of a compound of formula (I), which process comprises treating a compound of formula (II) or a salt thereof:

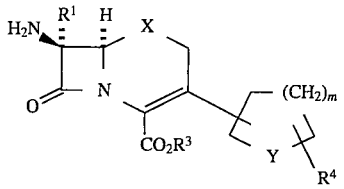

wherein $R^1$, $CO_2R^3$, $R^4$, m, X and Y are as hereinbefore defined, wherein any reactive groups may be protected, and wherein the amino group is optionally substituted with a group which permits acylation to take place; with an N-acylating derivative of an acid of formula (III):

$$R^2OH \quad (III)$$

wherein $R^2$ is as defined with respect to formula (I) and wherein any reactive groups may be protected; and thereafter, if necessary or desired, carrying out one or more of the following steps:
  i) removing any protecting groups;
  ii) converting the group $CO_2R^3$ into a different group $CO_2R^3$;
  iii) converting the group $R^2$ into a different group $R^2$;
  iv) converting the group X into a different group X;
  v) converting the product into a salt.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula —$P.R^{20}R^{21}$ wherein $R^{20}$ is an alkyl, haloalkyl, aryl, aralkyl, alkoxy, haloalkyl, aryl, aralkyl, alkoxy, haloalkoxy, aryloxy, aralkyloxy or dialkylamino group, $R^{21}$ is the same as $R^{20}$ or is halogen or $R^{20}$ and $R^{21}$ together form a ring; suitable such phosphorus groups being —$P(OC_2H_5)_2$, —$P(C_2H_5)_2$,

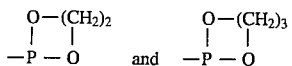

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl)acetamide, N,O-bis(trimethylsilyl)- trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30°–60° C., preferably 40°–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an add halide, preferably the add chloride or bromide or alternatively a symmetrical or mixed anhydride. The acylation may be effected in the presence of an add binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with add halide or anhydride is suitably carried out in the presence of a basic catalyst such as pyridine or 2,6-lutidine.

Acid halides may be prepared by reacting the acid (III) or a salt or a reactive derivative thereof with a halogenating (e.g. chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimlde, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexyl-carbodiimide, or N-ethyl-N'-[3-(dimethylamino)propyl]- carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the add of formula (III) is to treat the add of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an add binding agent such as pyridine. A catalyst such as 4-dimethylaminopyridine may optionally also be added. A preferred solvent for the above acylation reaction is dichloromethane. The optional reduction step, the optional conversion of $R^2$ to a different $R^2$, $CO_2R^3$ to a different $CO_2R^3$ and X to a different X, Y to a different Y, and the optional formation of a salt, may be carded out using methods well known in the art of cephalosporin and penicillin chemistry.

For example, when the group X is S, SO, or $SO_2$, the group X may be converted into a different group X by methods of oxidation or reduction well known in the art of cephalosporin and penicillin synthesis, as described, for example, in European Patent Application Publication No. 0 114 752. Equally, when the group Y is S, SO, or $SO_2$, the group Y may be converted into a different group Y by similar methods. For example, sulphoxides (in which X or Y is SO) may be prepared from the corresponding sulphide (in which X or Y is S) by oxidation with a suitable oxidising agent, for example an organic peracid such as m-chloroperbenzoic acid.

A reduction step is generally effected by processes well known in the art of β-lactam chemistry, for example using phosphorus trichloride in dimethylformamide.

In the process described hereinabove, and in the process described hereinbelow, it may be necessary to remove protecting groups. Deprotection may be carded out by any convenient method known in the art such that unwanted side reactions are minimised. Separation of unwanted by-products may be carried out using standard methods.

In a further process of the invention, compounds of formula (I) may be prepared by cyclising a compound of formula (IV):

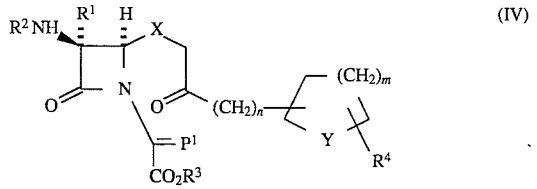
(IV)

wherein X, $R^1$, $R^2$, $R^4$, and m, and $CO_2R^3$ are as hereinbefore defined and P' is a phosphorus residue; and thereafter if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) converting the product into a salt.

The cyclisation reaction is an intramolecular Wittig-type reaction and is typically carried out by heating the compound of formula (IV) in an organic solvent system, for example in toluene, optionally in the presence of a suitable add such as benzoic add.

The phosphorus residue, P' is typically a trialkylphosphoranylidene residue, for example a $C_{1-6}$ trialkylphosphoranylidene residue such as tri-n-butylphosphoranylidene, or a triarylphosphoranylidene residue such as triphenylphosphoranylidene.

Where $R^2$ in a compound of formula (I) is required to be different from the group $R^2$ in the compound of formula (IV), the conversion may be effected via the intermediacy of a compound of formula (II) which has an amino group at the 7-position of the cephalosporin nucleus.

An $R^2$ acyl side-chain may be removed by the Delft procedure commonly used in β-lactam chemistry. Suitable reaction conditions include treatment with phosphorus pentachloride and N-methylmorpholine at reduced temperature.

Compounds of formula (II) are novel compounds and as such form part of the invention.

A compound of formula (IV) may be prepared from a compound of formula (V):

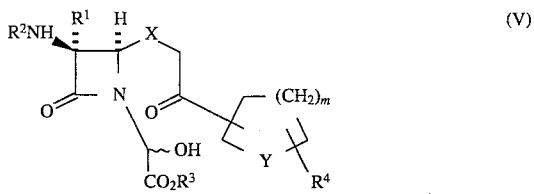
(V)

wherein X, $R^1$, $R^2$, $R^4$, m, and $CO_2R^3$ are as hereinbefore defined, by reaction with a halogenating agent, suitably a chlorinating agent such as thionyl chloride, which reaction displaces the formula (V) hydroxyl group by halogen, suitably chloride, and is typically carried out at reduced temperature in an inert solvent, for example in tetrahydrofuran, in the presence of a base, typically a pyridine derivative such as 2,6-lutidine. Formation of the phosphorane may be effected by treatment of the halo-intermediate with an appropriate phosphine derivative, for example tri-n-butylphosphine or triphenylphosphine, suitably at ambient temperature in an inert solvent such as dioxan.

A compound of formula (V) may be prepared by reaction of a compound of formula (VI):

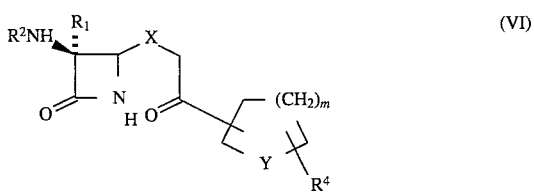
(VI)

wherein X, $R^1$, $R^2$, $R^4$, and m are as hereinbefore defined with an ester of glyoxylic acid ($OCHCO_2R^3$) in the presence of triethylamine.

In a typical preparation of a compound of formula (VI) in which X is sulphur, a compound of formula (VII):

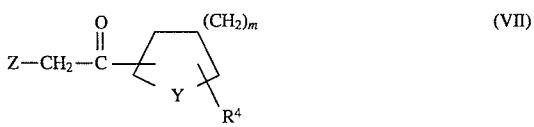
(VII)

wherein Z is a leaving group and $R^4$, and m are as hereinbefore defined is reacted with a compound of formula (VIII):

(VIII)

wherein $R^1$ and $R^2$ are as hereinbefore defined.

Suitably, a leaving group Z is halogen, for example chloro. The reaction may be carried out at ambient temperature in an inert solvent, for example acetone or dimethylformamide, in the presence for a base, for example potassium carbonate.

A compound of formula (V) may also be prepared by reaction of a compound of formula (IX):

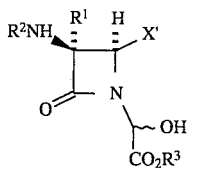

wherein $R^1$, $R^2$ and $CO_2R^3$ are as hereinbefore defined and X' is an X-group precursor, with a compound of formula (VII) as hereinbefore defined.

In a typical preparation of a compound of formula (V) in which X is sulphur, a Z leaving group in a compound of formula (VII), suitably a halogen such as chloro or bromo, is displaced by an X' mercapto group in a compound of formula (IX). The reaction may be carried out at ambient temperature in an inert solvent, for example acetone, with the addition of base, for example potassium carbonate, before work-up.

Azetidin-2-one compounds of formulae (VIII) and (IX) may be prepared according to known methods in heterocyclic synthetic chemistry and particularly by known methods in the art of β-lactam chemistry. For example a compound of formula (VIII) may be prepared according to the method of Osborne N. F. et al., J. Chem. Soc., Perkin Trans. I, 146, 1980.

A compound of formula (IX) in which X' is a mercapto group may be prepared by ring opening of a 4-thia-2,6-diazabicyclo [3.2.0]-hept-2-ene-7-one derivative according to the method of Masayuki Narisada et al., Tetrahedron Lett., 1755 (1978).

Compounds of formula (VII) are known compounds or may be prepared by standard methodology. For example, the compounds of formula (VII) in which Y is chloro or bromo may be prepared from the corresponding carboxylic add (Y=COOH) via formation of the acid chloride followed by treatment with diazomethane and reaction of the resulting diazo compound with hydrogen chloride or hydrogen bromide.

In a further process of the invention, compounds of formula (I) may be prepared directly by organo-cuprate displacement of a leaving group at the 3-position of a compound of formula (X):

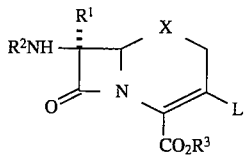

wherein $R^1$, $R^2$, $CO_2R^3$ and X are as hereinbefore defined and L is a leaving group, suitably a mesylate, triflate or fluorosulphonate leaving group, by reaction with a compound of formula (XI):

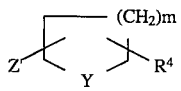

wherein Z' is an organo-cuprate group and $R^4$ and m are as hereinbefore defined.

A compound with a 3-position leaving group, L, in which X is sulphur may be prepared by the procedure of Farina V. et al., J. Org. Chem., 54, 4962, (1989).

A compound with a 3-position leaving group, L, in which X is $CH_2$ may be prepared by a transition metal-catalysed carbenoid insertion reaction of a diazodicarbonyl compound of formula (XII):

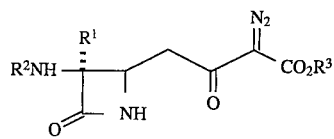

wherein $R^1$, $R^2$ and $CO_2R^3$ are as hereinbefore defined, followed by reaction with an appropriate anhydride, for example triflic anhydride.

Compounds of formula (XII) may be prepared by the procedure of Bodurow C. and Carr M. A.; Tetrahedron Lett., 30 4801, (1989).

It should be noted that in processes of this invention $\Delta^2$-cephems may function as intermediates, in the synthetic sequences. Subsequent isomerisation steps by methods well known in cephalosporin chemistry will provide the $\Delta^3$-cephems of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carders, such as cream or ointment bases and ethanol or oleyl alcohol for lotions. Such carders may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen afar filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (XIII) or a pharmaceutically acceptable salt or ester thereof:

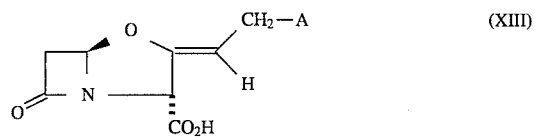
(XIII)

wherein

A is hydroxyl, substituted hydroxyl, thiol, substituted thiol, amino, mono- or di-hydrocarbyl- substituted amino, or mono- or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (XIV) or a pharmaceutically acceptable salt or in vivo hydrolysable ester thereof:

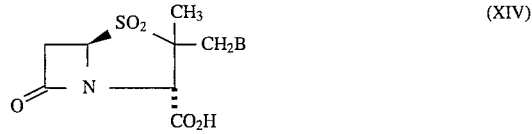
(XIV)

wherein

B represents hydrogen, halogen or a group of formula:

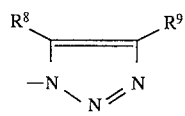

in which $R^8$ and $R^9$ are the same or different and each represents hydrogen, $C_{1-6}$ alkoxycarbonyl or carboxy, or a pharmaceutically acceptable salt thereof.

Further suitable β-lactamase inhibitors include 6-alkylidene penems of formula (XV):

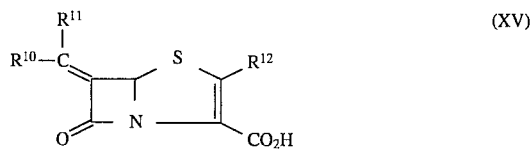
(XV)

or a pharmaceutically acceptable salt or in vivo hydrolysable ester thereof, wherein $R^{10}$ and $R^{11}$ are the same or different and each represents hydrogen, or a $C_{1-10}$ hydrocarbon or heterocyclic group optionally substituted with a functional group; and $R^{12}$ represents hydrogen or a group of formula $R^{13}$ or $-SR^{13}$ where $R^{13}$ is an optionally substituted $C_{1-10}$ hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as E. coli and Gram-positive organisms such as S. aureus.

The following Examples illustrate the preparation of compounds of the invention and intermediates thereto.

EXAMPLE 1

Sodium (6R,7R)-7-[2-(2-Aminothiazol-4-yl)-2-(Z)-methoxyiminoacetamido]-3-[(RS)-tetrahydrothien-2-yl]cheph-3-em-4-carboxylate (a) (RS)-2-Chloroacotyltetrahydrothiophene (RS)-2-Tetrahydrothiophene carboxylic acid (6.47 g) in dichloromethane (100 ml) was treated at room temperature with 2–3 drops of DMF followed by oxalyl chloride (18 g, 12.37 ml). After ca. 2 h a sample showed no remaining acid ($v_{max}$ 1780 cm$^{-1}$). The solvent and excess oxalyl chloride were removed under reduced pressure. Addition of a further 50 ml of dichloromethane and re-evaporation gave the crude acid chloride. The add chloride in dichloromethane (50 ml), was added dropwise, to a solution of diazomethane (90 mM) in ether (200 ml) cooled in ice/water. After complete addition the solvent was removed in vacuo and ether (200 ml) added. The solution was filtered through celite, cooled to −10° C. and hydrogen chloride bubbled slowly through the solution. As soon as t.l.c. (4% ethyl acetate/hexane) showed no starting material the reaction mixture was decanted, washed once with brine, dried and concentrated. Flash chromatography on silica gel with 5% ethyl acetate/hexane afforded the title compound as a pale yellow crystalline solid, unstable at room temperature, (5.394 g, 67%); (Found: M$^+$, 164.0064. C$_6$H$_9$ClOS requires M, 164.0063); $v_{max}$ (CH$_2$Cl$_2$) 1731 cm$^{-1}$; $\delta_H$ (CDCl$_3$) 1.85–1.98 (1H, m), 2.05–2.16 (2H, m), 2.40–2.50 (1H, m), 2.91 (2H, m), 4.24 (1H, m) and 4.26 and 4.33 (2H, ABq, J 15.3 Hz).

(b) (3R,4R)-3-Phenoxyacetamido-4-[(RS)-tetrahydrothien-2-yl-carbonylmethylthio]azetidin-2-one (RS)-2-Chloroacetyltetrahydrothiophene (2.50 g), (3R,4R)-4-mercapto-3-phenoxyacetamidoazetidin-2-one (4.60 g) and potassium carbonate (2.52 g) in DMF (30 ml) were stirred at room temperature for 2.5 h. T.l.c. analysis (ethyl acetate) showed completion of the reaction. The reaction mixture was diluted with ethyl acetate, washed with water (3×), brine and then dried. The solvent was evaporated and the residue flash chromatographed on silica gel eluting with 80% ethyl acetate/hexane to give the title compound as a pale yellow solid (4.194 g, 73%); m.p. 123° C., ethyl acetate/hexane; (Found: C, 53.51; H, 5.00; N, 7.39; S, 17.06%. C$_{17}$H$_{20}$N$_2$O$_4$S$_2$ requires C, 53.66; H, 5.30; N, 7.36; S, 16.85%); $v_{max}$ (CH$_2$Cl$_2$) 3405, 1785 and 1695 cm$^{-1}$; $\delta_H$ (CDCl$_3$), 1.81–1.95 (1H, m), 2.01–2.12 (2H, m), 2.28–2.42 (1H, m), 2.88 (1H, t, J 6.5 Hz), 3.39 and 3.56 with 3.39 and 3.45 (2H, 2 ABq, J 5.9 Hz), 4.07 and 4.09 (1H, 2 t, J 3.8 and 3.7 Hz), 4.58 (2H, s), 5.00 and 5.04 (1H, 2d, J 4.6 Hz), 5.58 and 5.60 (1H, 2 dd's, J 4.6, 9.2 Hz), 6.55 and 6.64 (1H, 2 br s), 6.94–7.07 (3H, m), 7.27–7.36 (2H, m), and 7.46 and 7.47 (1H, 2 br d, J 9.2 Hz).

(c) t-Butyl (RS)-2-Hydroxy-2-[(3R,4R)-3-phenoxyacetamido-4-[(RS)-tetrahydrothein-2-ylcarbonylmethylthio]azetidin-2-on-1-yl]acetate 1M t-Butyl glyoxylate in 1,2-dichloroethane (20 ml) was added to a solution of (3R,4R)-3-phenoxyacetamido-4-[(RS)-tetrahydrothien-2-ylcarbonylmethylthio]azetidin-2-one (4.194 g) in 1,2-dichloroethane (30 ml) followed by triethylamine (0.111 g, 0.153 ml), and stirred for 2 h at room temperature, until reaction complete by t.l.c. (ethyl acetate). The solution was concentrated and flash chromatographed on silica gel eluting with 70, 80 and 90% ethyl acetate/hexane to give the title compound as a yellow foam (4.597 g, 82%); $v_{max}$ (CH$_2$Cl$_2$) 3492, 3408, 1782, 1736 and 1695 cm$^{-1}$; $\delta_H$ (CDCl$_3$) 1.33, 1.34 and 1.35 (9H, 3s), 1.76–1.90 (1H, m), 2.00–2.13 (2H, m), 2.28–2.44 (1H, m) 2.86 (2H, m), 3.32–3.73 (2H, m), 4.02–4.13 (1H, m) 4.59 (2H, s), 5.05, 5.07, 5.14 and 5.15 (1H, 4d's, J 4.8, 4.9, 4.7 and 4.8 Hz), 5.23–5.41 (1H, m), 5.45 and 5.60 (1H, m), 6.94–7.07 (3H, m) and 7.27–7.60 (3H, m).

(d) t-Butyl 2-[(3R,4R)-3-Phenoxyacetamido-4-[(RS)-tetrahydrothien-2-ylcarbonylmethylthio]azetidin-2-on-1]-2-tri-n-butylphosphoranylideneacetate t-Butyl (RS)-2-hydroxy-2-[(3R,4R)-3-phenoxyacetamido-4-[(RS)-tetrahydrothien-2-ylcarbonylmethylthio]azetidin-2-on-1-yl]acetate (4.58 g) in dry THF (20 ml) under an atmosphere of argon was cooled to −20° C. and treated with 2,6-lutidine. A solution of thionyl chloride (1.6 g, 0.97 ml) in dry THF (10 ml) was added dropwise while stirring. After complete addition, the reaction mixture was allowed to warm to 0° C. for ca. 30 min. T.l.c. (ethyl acetate) showed no starting material. The mixture was filtered and the solvent evaporated. The resultant oil was redissolved in dry dioxan (30 ml) and tri-n-butylphosphine (3.99 g, 4.91 ml) was added in one portion. After 15 min at room temperature t.l.c. (ethyl acetate) showed the completion of the reaction. The solution was diluted with ethyl acetate, washed with water (3×), brine and dried. Air removal of solvent in vacuo the residue was flash chromatographed on silica gel using 50, 70 and then 90% ethyl acetate/hexane to give the title compound as an orange gum (2.969 g, 48%); $v_{max}$ (CH$_2$Cl$_2$) 3416, 1764, 1691, 1626 and 1601 cm$^{-1}$; [mass spectrum: +ve ion (3NOBA, Na$^+$) MH$^+$ (695), MNa$^+$ (717)].

(e) t-Butyl (6R,7R)-7-Phenoxyacetamido-3-(tetrahydrothien-2-yl)ceph-3-em-4-carboxylate t-Butyl 2-[(3R,4R)-3-phenoxyacetamido-4-[(RS)-tetrahydrothien-2-yl carbonylmethylthio]azetidin-2-on-1-yl]-2-tri-n-butylphosphoranylideneacetate (2.96 g) in toluene (100 ml) was heated under reflux for ca. 24 h. T.l.c. showed very small amounts of unchanged starting material. The solution was concentrated and flash chromatographed on silica gel eluting with 30, 40, 50 and 60% ethyl acetate/hexane. The first product to be eluted was the high Rf single diastereoisomer of the title compound (0.388 g, 19%) as a yellow foam; (Found: M$^+$, 476.1442. C$_{23}$H$_{28}$N$_2$O$_5$S$_2$ requires M, 476.1440); $v_{max}$ (CH$_2$Cl$_2$) 3407, 1783, 1716 and 1698 cm$^{-1}$; $\Delta_H$ (CDCl$_3$) 1.45–1.63 (10H, s overlapping m), 1.82–2.01 (1H, m), 2.21–2.33 (1H, m), 2.44–2.53 (1H, m), 2.97 (1H, dd, J 3.9, 8.8 Hz), 3.35 and 3.76 (2H, ABq, J 18.0 Hz), 4.57 (2H, s), 4.90 and 4.94 (1H, dd, J 6.5, 9.9 Hz), 5.01 (1H, d, J 4.8 Hz), 5.86 and 5.91 (1H, dd, J 4.8, 9.3 Hz), 6.85–7.07 (3H, m) and 7.24–7.36 (3H, m). The second product to be eluted was contaminated with an impurity. Re-chromatography of this material afford the low Rf diastereoisomer of the title compound (0.428 g, 21%); $v_{max}$ (CH$_2$Cl$_2$) 3406, 1785, 1719 and 1697 cm$^{-1}$; $\delta_H$ (CDCl$_3$) 1.45–2.00 (11H, m overlapping s), 2.93–2.98 (2H, m), 3.45 and 3.56 (2H, ABq, J 17.3 Hz), 4.57 (2H, s), 4.84 (1H, dd, J 6.3, 10.0 Hz), 5.03 (1H, d, J 4.9 Hz), 5.88 (1H, dd, J 4.9, 12.7 Hz), 6.91–7.07 (3H, m) and 7.25–7.36 (3H, m).

(f) (i) t-Butyl (6R,7R)-7-Amino-3-( tetrahydrothien-2-yl)-ceph-3-em-4-carboxylate t-Butyl (6R, 7R)-7-phenoxyacetamido-3-(tetrahydrothien-2-yl)ceph-3-em-4-carboxylate (0.375 g), high Rf diastereoisomer in dry dichloromethane (5 ml) was cooled to −20° C. under argon and treated with N-methylmorpholine (0.175 g, 0.19 ml). A solution of phosphorous pentachloride (0.214 g) in dichloromethane (5.3 ml) was added. After 30 min. a sample showed no starting material (by i.r.). Methanol (3 ml) was added rapidly in one portion and then allowed to warm to room temperature. After 1 h water (5 ml) was added and the solution vigorously stirred for 30 min. The solvent was removed in vacuo and ethyl acetate added. The pH was adjusted to 7 with concentrated aqueous ammonia solution. Flash chromatography on silica gel with 50 and 60% ethyl acetate/hexane gave the more mobile diastereoisomer of the title compound as a pale yellow foam (0.104 g, 39%); (Found: M$^+$, 342.1081. C$_{15}$H$_{22}$N$_2$O$_3$S$_2$ requires M, 342.1072); $v_{max}$ (CH$_2$Cl$_2$) 1776 and 1716 cm$^{-1}$; $\delta_H$ (CDCl$_3$) 1.56 (10H, s overlapping m), 1.79–1.99 (3H, m collapses to 1H, m on D20), 2.22–2.33 (1H, m), 2.42–2.53 (1H, m), 2.98 (2H, dd, J 4.0, 8.9 Hz), 3.36 and 3.74 (2H, ABq, J 17.9 Hz), 4.73 and 4.93 (2H, ABq, J 5.0 Hz) and 4.88 (1H, dd, J 6.5, 9.9 Hz). The second, more polar diastereoisomer of the title compound, was obtained as a pale yellow solid (0.079 g, 29%); (Found: M$^+$, 342.1085. C$_{15}$H$_{22}$N$_2$O$_3$S$_2$ requires M, 342.1072); $v_{max}$ (CH$_2$Cl$_2$) 1777 and 1718 cm$^{-1}$; $\delta_H$ (CDCl$_3$) 1.57 (9H, s), 1.66–2.99 (4H, m collapses to 2H, m on D20), 2.03–2.14 (1H, m), 2.23–2.35 (1H, m), 2.96 (2H, dd, J 4.2, 8.6 Hz), 3.43 and 3.75 (2H, ABq, J 17.1 Hz), 4.69 and 4.96 (2H, ABq, J 5.0 Hz) and 4.79 (1H, dd, J 6.1, 9.9 Hz).

(ii) t-Butyl (6R,7R)-7-amino-3-(tetrahydrothien-2-yl)-ceph-3-em-4-carboxylate (0.4 g), low Rf diastereoisomer was treated with phosphorus pentachloride (0.228 g) in dichloromethane (5.69 ml) then methanol and water as described in Example f(i). After purification by flash chromatography the title compound, as a mixture of diastereoisomers (by t.l.c., n.m.r.) was obtained as a yellow foam (0.188 g, 65%).

(g) t-Butyl (6R,7R)-7-[2-(Z)-Methoxyimino-2-(2-tritylaminothiazol,4-yl)acetamido]-3,(tetrahydrothien-2-yl)ceph-3-em-4-carboxylate Mesyl chloride (0.125 g, 0.085 ml) was added to 2-(Z)-methoxyimino-2-(2-tritylaminothiazol-4-yl)acetic acid hydrochloride (0.524 g) and diisopropylethylamine (0.282 g, 0.38 ml) in DMF (4 ml), under argon at −50° C. for 1 h. t-Butyl (6R,7R)-7-amino-3-(tetrahydrothien-2-yl)ceph-3-em-4-carboxylate (0.34 g) in DMY (5 ml) and pyridine (0.1 g, 0.102 ml) were added and the solution allowed to warm to room temperature over 1–2 h. The reaction mixture was diluted with ethyl acetate, washed with water (3×), brine and dried. Concentration and flash chromatography on silica gel eluting with 30, 40 and 50% ethyl acetate/hexane afforded initially the least polar isomer of the title compound, as a yellow foam, (0.173 g, 23%); $v_{max}$ ($CH_2Cl_2$) 3395, 1783, 1717, 1684 and 1520 $cm^{-1}$; $\delta_H$ ($CDCl_3$), 1.53 (10H, s overlapping m), 1.84–1.98 (1H, m), 2.21–2.35 (1H, m), 2.53–2.93 (1H, m), 2.95–3.00 (2H, m), 3.36 and 3.75 (2H, ABq, J 18.0 Hz), 4.08 (3H, s), 4.93 (1H, dd, J 6.5, 9.8 Hz), 5.03 (1H, d, J 4.8 Hz), 5.90 (1H, dd, J 4.8, 8.7 Hz collapses to d, J 4.8 Hz on $D_2O$) 6.72–6.76 (2H, m collapses to 1H, s on $D_2O$), 7.02 (1H, br s, exchangeable with $D_2O$) and 7.32 (15H, s); [mass spectrum: +ve ion (3NOBA, $Na^+$) $MNa^+$ (790)]. Also eluted was a mixture of diastereoisomers (0.132 g, 17%) followed by the more polar isomer of the title compound as an orange gum (0.259 g, 34%); $v_{max}$ ($CH_2Cl_2$) 3395, 1784, 1718, 1687 and 1519 $cm^{-1}$; $\delta_H$ ($CDCl_3$) 1.57 (9H, s), 1.65–2.02 (2H, m), 2.03–2.15 (1H, m), 2.22–2.36 (1H, m), 2.91–2.99 (1H, m), 3.44–3.74 ($2_H$, ABq, J 17.3 Hz), 4.08 (3H, br s, sharpens on $D_2O$), 4.85 (1H, dd, J 6.2, 9.9 Hz), 5.06 (1H, d, J 4.8 Hz), 5.87 (1H, dd, J 4.8, 8.8 Hz collapses to d, J 4.8 Hz on $D_2O$), 6.75 (2H, br s collapses to 1H, s on $D_2O$), 7.02 (1H, br s exchangeable with $D_2O$) and 7.32 (15H, s); [mass spectrum: +ve ion (3NOBA, $Na^+MNa^+$, (790)].

(h) Sodium (6R,7R)-7-[2-(2-Aminothiazol-4-yl)-2-(Z)-methoxyiminoacetamido]-3-[(RS)-tetrahydrothien-2-yl]ceph-3-em-4-carboxylate t-Butyl (6R,7R)-7-[2-(Z)-methoxyimino-2-(2-tritylaminothiazol-4-yl)acetamide]-3-(tetrahydrothien-2-yl)ceph-3-em-4-carboxylate, (0.54 g) in a solution of 1M aqueous hydrochloric acid (0.704 ml) and 98% formic acid (6.34 ml) was maintained at ambient temperature for 1 h, then 4 drops of conc. hydrochloric acid was added. After a further 30 min., the solution was filtered and the precipitate washed with formic acid. The solvent was removed in vacuo and the residual foam dissolved in aqueous sodium hydrogen carbonate at pH8. The solution was chromatographed on HP20SS resin eluting with portions of 0, 2, 4 and 6% tetrahydrofuran/water. The product, collected as an aqueous solution was concentrated and freeze-dried to give the title compound as a pale yellow amorphous solid, (0.268 g, 78%); $v_{max}$ (KBr) 1757, 1669 and 1597 $cm^{-1}$; $\delta_H$ ($CD_3$)$_2SO$) 1.55–1.76 (2H, m), 1.88 and 2.15 (2H, 2m's), 2.74–2.94 (2H, 3.27 and 3.53 with 3.42 and 3.53 (2H, 2ABq's, J 16.7 and 16.4 Hz), 3.84 (3H, s), 4.98 and 5.03 (1H, 2d's, J 4.7 and 4.7 Hz), 5.07 and 5.15 (1H, 2m's 5.50 and 5.52 (1H, 2dd's, J 4.4, 8.4 and 4.2, 8.4 Hz, collapses to 2d's, J 4.7 and 4.2 hz), 8.76 (1H, s), 7.26 (2H, s, exchangeable on $D_2O$), 9.50 and 9.52 (1H, 2d's, J8.4 and 8.4 Hz, exchangeable on $D_2O$); [mass spectrum: +ve ion (thioglycerol) $MH^+$ (492), $MNa^+$ (514)].

EXAMPLE 2

Pivaloyloxymethyl (6R,7R)-7-[2-(2-Aminothiazol-4-yl)-2-(Z)-methoxy-iminoacetamido]-3-[(RS)-tetrahydrothien-2-yl]ceph-3-em-4-carboxylate Pivaloyl bromide (0.149 g) in acetone (2 ml) under an atmosphere of argon, was stirred with sodium iodide (0.114 g) for 30 min. The solution was filtered and evaporated. The residue was stirred with toluene (2 ml) and added to a suspension of sodium (6R,7R)-7-[2-(2-aminothiazol-4-yl)-2-(Z)methoxyiminoacetamido]-3-[(RS)-tetrahydrothien-2-yl]ceph-3-em-4-carboxylate (0.17 g) in N-methylpyrrolidinone (2 ml) at room temperature for 30 min. The reaction mixture was diluted with ethyl acetate, washed with water, brine and dried. After concentration, the residue was flash chromatographed on silica gel, eluting with ethyl acetate to give the title compound as a pale yellow foam, (0.082 g, 41%); $v_{max}$ ($CH_2Cl_2$) 3486, 3389, 1786, 1751, 1736, 1688 and 1606 $cm^{-1}$; $\delta_H$ ($CDCl_3$) 1.25 (9H, s), 1.55–2.53 (4H, m), 2.98 (2H, m), 3.94 and 3.79 with 3.49 and 3.84 (2H, 2ABq's, J 17.8 and 17.2 Hz), 4.14 (3H, s), 4.91 (1H, m), 5.08 and 5.10 (1H, 2d's, J 4.8 and 4.7 hz), 5.84–5.98 (3H, m), 6.24 (1H, br m, exchangeable with $D_2O$), 7.06 (1H, s) and 7.43 (1H, m, exchangeable with $D_2O$); [mass spectrum: +ve ion (3NOBA, $Na^+$) $MNa^+$ (606)].

EXAMPLE 3

Sodium (6R,7R)-7-[2-(2-Aminothiazol-4-yl)-2-(Z)-methoxyimino-acetamido]-3-(1,1-dioxotetrahydrothien-2-yl)ceph-3-em-4-carboxylate (a) 4-Methoxybenzyl (6R,7R)-7-Phenylacetamido-3-(1,1-dioxotetrahydrothien-2- yl )ceph-2-em-4-carboxylate Sulpholane (0.077 g) in dry THF (2 ml) under argon was cooled in an ice-bath and treated, dropwise, with n-butyl-lithium. The ice-bath was removed and the solution warmed to room temperature and stirred for 10 min. to give a yellow solution.

Copper (II) bromide-dimethyl sulphide complex (0.066 g) in THF (1 ml) and dimethyl sulphide (1 ml), under argon was cooled to −78° C. and treated with the lithiated sulpholane via syringe in a dropwise fashion.

After 30 min. a solution of 4-methoxybenzyl (6R,7R)-7-phenylacetamido-3-trifluoromethanesulphonyloxyceph-3-em-4-carboxylate, (0.25 g) (prepared according to the procedure described by V. Farina et al, J. Org. Chum., 1989, 54, 4962), in dry THF (2 ml) was added and the solution stirred at −78° C. for a further 30 min. The reaction mixture was then quenched with saturated ammonium chloride (3 ml s) and warmed to room temperature. After dilution with ethyl acetate and washing with water, brine and drying, the crude product was flash chromatographed on silica gel, eluting with 50, 60, 70 and 80% ethyl acetate-hexane. The title compound was obtained as a mixture of isomers as a colourless foam, (0.133 g, 56%); $v_{max}$ ($CH_2Cl_2$) 3413, 1782, 1743, 1687, 1613 and 1515 cm$^{-1}$; $\delta_H$ ((CD$_3$)$_2$SO) 1.90–2.29 (4H, m), 2.93–3.21 (2H, m), 3.63 (2H, s), 3.82 (3H, s), 4.93 and 5.05 (1H, 2s), 7.58 and 7.66 (1H, 2d, J 2.9 Hz), 5.17–5.23 (2H, m), 5.59 (1H J 2.9, 7.6Hz), 6.25 and 6.38 (1H, 2d, J 7.6Hz), 6.37 and 6.49 (1H, 2s), 6.89 (2H, d, J 8.1 Hz) and 7.26–7.40 (7H, m); [mass spectrum: +ve ion (3-NOBA, Na$^+$) MNa$^+$ (579)].

(b) 4-Methoxybenzyl (6R,7R)-1-Oxo-7-phenylacetamido-3-(1,1-dioxotetrahydrothien-2-yl)ceph-3-em-4-carboxylate 4-Methoxybenzyl (6R, 7R)-7-phenylacetamido-3-(1,1-dioxotetrahydrothien-2-yl)ceph-2-em-4-carboxylate (0.973 g) in dichloromethane (20 ml) was cooled in ice-water and treated with 3-chloroperbenzoic acid (0.343 g) and warmed to room temperature for 1 h. The solution was washed with saturated sodium metabisulphite, brine and then dried. Afar removal of solvent, the residue was flash chromatographed on silica gel eluting initially with 80, 90% ethyl acetate-hexane and then ethyl acetate. The first product eluted was the least polar isomer of the title compound, obtained as a pale yellow foam, (0.309 g, 31%); $\delta_H$ (CDCl$_3$) 2.02–2.39 (4H, m), 2.91–3.03 (1H, m), 3.11–3.20 (1H, m), 3.49 and 3.79 (2H, ABq, J 8.6 Hz), 3.58 and 3.66 (2H, ABq, J 15.9 Hz), 3.81 (3H, s), 4.52 (1H, d, J 4.7 Hz), 5.02 (1H, dd, J 7.3, 11.2 Hz), 5.20 and 5.26 (2H, ABq, J 11.4 Hz), 6.03 (1H, dd, J 4.7, 10.0 hz), 6.69 (1H, d, J 10.0 Hz), 6.90 (2H, d, J 8.7 Hz) and 7.26–7.39 (7H, m). Further elution with 10% ethanol-ethyl acetate provided the second more polar isomer as an off white, amorphous solid, (0.166g, 17%); $\delta_H$ (CDCl$_3$) 1.90–2.30 (4H, m), 2.88–3.20 (2H, m), 3.06 a 4.13 (2H, ABq, J 18.4 Hz), 3.57 (2H, s), 3.77 (3H, s), 4.43 (1H, d, J 4.1 Hz), 4.61 (1H, t, J 8.3 Hz), 5.18 (3H, m), 5.98 (1H, dd J 4.8, 9.6 Hz), 6.84 (2H, d, J 8.7 Hz) and 7.17–7.36 (7H, m).

(c) 4-Methoxybenzyl (6R,7R)-7-Phenylacetamido-3-(1,1-dioxotetrahydrothien-2-yl)ceph-3-em-4-carboxylate (i) The more polar isomer of 4-methoxybenzyl (6R,7R)-1-oxo-7-phenylacetamido-3-(1,1-dioxotetrahydrothien-2-yl)-ceph-3-em-4-carboxylate, (0.166 g) in dry DMF (1 ml), under argon was cooled to −30° C. and treated with phosphorus trichloride for 10 min. The reaction mixture was diluted with ethyl acetate, washed with water (3x), brine and then dried. Removal of the solvent and purification by flash chromatography on silica gel, gave the more polar isomer of the title compound as an off white foam (0.118 g, 73%); $\nu_{max}$ (CH$_2$Cl$_2$) 3410, 1789, 1726, 1688, 1613 and 1515 cm$^{-1}$; $\delta_H$ (CDCl$_3$) 2.07–2.31 (4H, m), 2.92–3.01 (1H, m), 3.20–3.30 (1H, m), 3.36 and 3.75 (2H, ABq, J 17.5 Hz), 3.62 (2H, s), 3.80 (3H, s), 4.74 (1H, t, J 9.7 Hz), 4.96 (1H, d, J 5.0 Hz), 5.21 (2H, s), 5.82 (1H, dd, J 5.0, 9.1 Hz), 6.36 (1H, d, J 9.1 Hz), 6.87 (2H, d, J 8.7 Hz) and 7.25–7.39 (7H, m); [mass spectrum: +ve ion (3-NOBA, Na$^+$) MNa$^+$ (579)].

(ii) The least polar isomer of 4-methoxybenzyl (6R,7R)-1-oxo-7-phenylacetamido-3-(1,1-dioxotetrahydrothien-2-yl)ceph-3-em-4-carboxylate, (0.309 g) in DMF (2 ml) was treated in the same way with phosphorus trichloride (0.152 g). After the same work up and purification least polar isomer of the title compound was obtained as a colourless foam, (0.237 g, 79%); $\nu_{max}$ (CH$_2$Cl$_2$) 3412, 1787, 1725, 1687, 1613 and 1516 cm$^{-1}$; $\delta_H$ (CDCl$_3$) 2.08–2.37 (4H, m), 2.94–3.06 (1H, m), 3.11–3.22 (1H, m), 3.31 and 3.80 (2H, ABq, J 18.4 Hz), 3.60 and 3.67 (2H, ABq, J 16.2 Hz), 3.80 (3H, s), 4.93 (1H, dd, J 6.9, 11.0 Hz), 5.01 (1H, d, J 4.9 hz), 5.15 and 5.22 (2H, ABq, J 11.3 Hz), 5.80 (1H, dd, J 4.9, 9.1 Hz), 6.09 (1H, d, J 9.1 Hz), 6.88 (2H, d, J 8.7 Hz) and 7.24–7.41 (7H, m); [mass spectrum: +ve ion (3-NOBA, Na$^+$) MNa$^+$ (579)].

(d) 4-Methoxybenzyl (6R,7R)-7-Amino-3-(1,1-dioxotetrahydrothien-2-yl)ceph-3-em-4-carboxylate The least polar isomer obtained in Example 3(a) (ii), (0.237 g) in dry dichloromethane (1 ml), under argon, was cooled to −20° C. and treated with 4-methylmorpholine (0.088 g) followed by a solution of phosphorus pentachloride (0.136 g) in dichloromethane (3.4 ml) in a dropwise fashion. The solution was warmed to −5° C. and maintained at that temperature for 30 min. Methanol (1 ml) was added in one portion and the reaction mixture warmed to room temperature over 30 min. Water (1 ml) was added and the mixture vigorously stirred for a further 30 min. The dichloromethane was evaporated under vacuum and replaced with ethyl acetate. The pH was adjusted to about 7 with 0.880 ammonia. The organic layer was separated and the aqueous phase extracted with ethyl acetate. The combined organic phases were washed once with brine, dried and concentrated to give a yellow gum. Purification by flash chromatography on silica gel afforded the title compound as a pale yellow foam, (0.14 g, 73%); (Found: M$^+$, 438.0917. C$_{19}$H$_{22}$N$_2$O$_6$S$_2$ requires M, 438.0919); $\nu_{max}$ (CH$_2$Cl$_2$) 3413, 1780, 1724, 1614 and 1516 cm$^{-1}$; $\delta_H$ (CDCl$_3$) 2.09–2.40 (4H, m), 2.96–3.08 (1H, m), 3.12–3.21 (1H, m), 3.40 and 3.83 (2H, ABq, J 18.2 Hz), 3.80 (3H, s), 4.76 (1H, d, J 5.0 Hz), 4.95 (1H, dd, J 7.1, 11.2 Hz), 5.02 (1H, d, J 5.0 Hz), 5.18 and 5.24 (2H, ABq, J 11.8 Hz), 6.89 (2H, d, J 8.7 Hz) and 7.34 (2H, d, J 8.7 Hz).

(e) 4-Methoxybenzyl (6R,7R)-7-[2-(Z)-methoxyiminothiazol-4-yl)-2-(Z)methoxyiminoacetamido]-3-(1,1-dioxotetrahydrothien-2-yl )ceph-3-em-4-carboxylate 2-(2-Aminothiazol-4-yl)-2-(Z)-methoxyiminoacetic acid, (0.07 g) in dry DMF (0.5 ml), under argon, was cooled to −50° C. and treated with diisopropylethylamine (0.045 g) followed by methanesulphonyl chloride (0.04 g). The mixture was maintained between −30° C. and −40° C. for 1 h. 4-Methoxybenzyl (6R,7R)-7-amino-3-(1,1-dioxotetrahydrothien-2-yl)ceph-3-em-4-carboxylate, (0.138 g), from Example 3(d) in DMF (0.5 ml) and pyridine (0.025 g) were then added and the reaction mixture allowed to warm to room temperature over 2 h. The solution was diluted with ethyl acetate, washed with water (2x), brine, dried and concentrated to a yellow foam. Flash chromatography on silica gel, eluting with 80, 90% ethyl acetate-hexane and then ethyl acetate gave the title compound as a pale yellow foam, (0.081 g, 41%); $\nu_{max}$ (CH$_2$Cl$_2$) 3481, 3387, 1784, 1727, 1684, 1613 and 1516 cm$^{-1}$; $\delta_H$ (CDCl$_3$) 2.10–2.42 (4H, m), 2.96–3.08 (1H, m), 3.15–3.23 (1H, m), 3.41 and 3.85 (2H, ABq, J 18.4 Hz), 3.81 (3H, s), 4.06 (3H, s), 4.99 (1H, dd, J 7.0, 11.5 Hz), 5.16 (1H, d, J 4.9 Hz), 5.21 (2H, s), 5.73 (2H, br s), 6.03 (1H, dd, J 5.0, 9.1 Hz), 6.81 (1H, s), 6.90 (2H, d, J 8.7 Hz), 7.33 (2H, d, J 8.7 Hz) and 7.84 (1H, d, J 9.1 Hz); [mass spectrum: +ve ion (3-NOBA, Na$^+$) MNa$^+$ (644)].

(f) Sodium (6R,7R)-7-[2-(2-Aminothiazol-4-yl)-2-(Z)-methoxyiminoacetamido]-3-(1,1-dioxotetrahydrothien-2-yl )ceph-3-em-4-carboxylate A solution of anisole (1 ml) in dichloromethane (1 ml) under argon, was cooled to −20° C. and treated with anhydrous aluminium chloride for 15 min. The mixture was further cooled to −40° C. and treated with a solution of the cephem from Example 3(e), (0.08 g) in dichloromethane (1.5 ml). After 5 min. 0.5M trisodium citrate (4 ml) was added and the reaction mixture warmed to room temperature for 15 min. The aqueous phase was separated, washed with dichloromethane and concentrated to a small volume. Chromatography on HP20SS afforded, after freeze-drying, the title compound as a pale yellow solid, (0.057 g, 85%); $\nu_{max}$ (KBr) 1762, 1664, 1610 and 1528 cm$^{-1}$; δ$_H$ ((CD$_3$)$_2$SO) 1.94 (1H, m), 2.15 (3H, m), 2.92–3.04 (1H, m), 3.07–3.16 (1H, m), 3.41 and 3.58 (2H, ABq, J 17.3 hz), 3.84 (3H, s), 5.08 (1H, d, J 4.9 Hz), 5.21 (1H, t, J 8.5 Hz), 5.57 (1H, dd, J 4.9, 8.2 Hz, collapses to d, J 4.9 Hz on D$_2$O), 6.74 (1H, s), 7.25 (2H, br s, exchangeable with D$_2$O) and 9.50 (1H, d, J 8.2 Hz, exchangeable on D$_2$O); [mass spectrum: +ve ion (thioglycerol) MH$^+$ (524), MNa$^+$ (546)].

(g) 4-Methoxybenzyl (6R,7R)-7-Amino-3-(1,1-dioxotetrahydrothien-2-yl)ceph-3-em-4-carboxylate The more polar isomer obtained in Example 3(b) (i), (0.534 g) in dry dichloromethane (2 ml), under argon was cooled to −20° C. and treated with 4-methylmorpholine (0.199 g) followed by phosphorus pentachloride (0.307 g) in dichloromethane (6.13 ml) as previously described in Example 3(d). The reaction was worked up with methanol (2 ml) and water (2 ml), as described, and the crude product purified in the same way. The title compound was obtained as a pale yellow solid, (0.231 g, 55%); (Found: M$^+$, 438.0917. C$_{19}$H$_{22}$N$_2$O$_6$S$_2$ requires M, 438.0919); ν$_{max}$ (CH$_2$Cl$_2$) 3417(w), 1782, 1726 1613 and 1516cm$^{-1}$; δ$_H$ (CDCl$_3$) 2.04–2.36 (4H, m), 2.94–3.07 (1H, m), 3.22–3.31 (1H, m), 3.41 and 3.81 (2H, ABq, J17.4 Hz), 3.82 (3H, s), 4.69 (1H, dd,J8.1, 10.5 Hz), 4.74 (1H, d, J5.0 Hz), 4.91 (1H, d, J5.0 Hz), 5.23 (2H, s), 6.89 (2H, d, J8.7 Hz) and 7.39 (2H, d, J8.7 Hz).

(h) 4-Methoxybenzyl (6R,7R)-7-[2-(2-Aminothiazol-4-yl)-2-(Z)methoxyiminoacetamido]-3-( 1,1-dioxotetrahydrothien-2yl )ceph-3-em-4-carboxylate 2-(2-Aminothiazol-4-yl)-2-(Z)-methoxyiminoacetic acid (0.106 g) in dry DMF (2 ml), was treated with diisopropylethylamine (0.069 g) at room temperature under argon and cooled to −50° C. The solution was then treated with methane- sulphonyl chloride (0.06 g) for 1 h., maintaining the temperature t −50° C. The product from example 3(g), (0.21 g) in DMF (2 ml) and pyridine (0.038 g) were added. The solution was warmed to room temperature over 2 h. The reaction mixture was worked up as described in example 3(e) and purified by flash chromatography on silica gel, eluting with 2% methanol-dichloromethane. The title compound was obtained as a pale yellow solid, (0.192 g, 64%); Γ$_{max\ (CH2}$Cl$_2$) 1789, 1726, 1687, 1610 and 1516cm$^{-1}$; δ$_H$ (CD$_3$)$_2$CO) 2.04–2.16 (1H, m), 2.31–2.47 (3H, m), 3.02–3.25 (2H, m), 3.67 and 3.80 (2H, ABq, J14.9 Hz), 3.84 (3H, s), 3.90 (3H, s), 4.68 (1H, dd, J 8.1, 10.5 Hz), 5.12 and 5.24 (2H, ABq, J 11.9 Hz), 5.22 (1H, d, J4.8 Hz), 5.97 (1H, dd, J4.8, 8.9 Hz), 6.62 (1H, s), 6.85 (1H, s), 6.94 (2H, d, J8.7 Hz), 7.41 (2H, d, J8.7 Hz) and 8.54 (1H, d, J8.9 Hz); [Mass Spectrum: +ve ion (thioglycerol), ME$^+$ (622)].

(i) Sodium (6R,7R)-7-[2-(2-Aminothiazol-4-yl)-2-(Z)methoxyiminoacetamido]-3-(1,1-dioxotetrahydrothien-2-yl)ceph-3-em-4-carboxylate Anisole (3 ml) and dichloromethane (3 ml), under argon were cooled to −20° C. and treated with aluminium chloride (0.118 g) for 15m. The solution was then further cooled to −40° C. and a solution of the cephalosporin (0.185 g) from example 3(h) in dichloromethane (3 ml) added. After 15m., 0.5M trisodium citrate (8 ml) was added. The reaction mixture was then worked up and purified as described in Example 3(f). The title compound was obtained as an amorphous white solid, (0.128 g, 82%); ν$_{max}$ (KBr) 1766, 1671, 1617 and 1529cm$^{-1}$; δ$_H$ ((CD$_3$)$_2$SO) 1.83–2.02 (1H, m), 2.06–2.20 (3H, m), 2.95–3.17 (2H, m), 3.46 (2H, s), 3.85 (3H, s), 5.03 (1H, d, J4.7 Hz), 5.38 (1H, t, J9.5 Hz), 5.54 (1H, dd, J4.7, 8.2 Hz collapses to d, J4.7 Hz with D$_2$O), 6.78 (1H, s), 7.25 (2H, br.s, exchangeable with D$_2$O) and 9.61 (1H, d, J8.2 Hz, exchangeable with D$_2$O); [mass spectrum: +ve ion (thioglycerol) MH$^+$ (502), MNa$^+$ (524)].

We claim:

1. A compound of formula (I) or a pharmaceutically acceptable salt thereof:

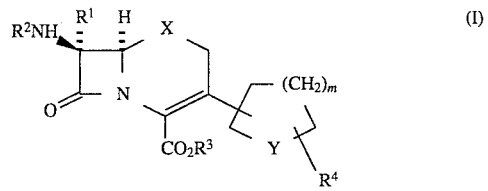

wherein R$^1$ is hydrogen, methoxy or formamido; R$^2$ is an acyl group of any one of the formulae (a) to (f):

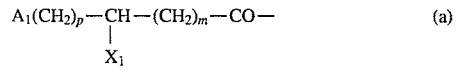

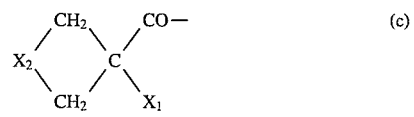

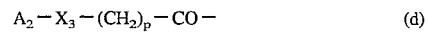

wherein p is 0, 1 or 2; m is 0, 1 or 2; A$_1$ is C$_{1-6}$alkyl, optionally substituted C$_{1-6}$alkyl, C$_{3-6}$cycloalkyl, cyclohexenyl, cyclohexadienyl, optionally substituted phenyl, thienyl, pyridyl, optionally substituted thiazolyl, C$_{1-6}$alkylthio or C$_{1-6}$alkyloxy; X$_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; A$_2$ is phenyl, 2,6-dimethoxyphenyl,2-alkoxy-1-naphthyl,3-arylisoxazolyl, or 3-aryl-5-methylisoxazolyl; a substituted C$_{1-6}$alkyl group; or a substituted dithietane; X$_2$ is —CH$_2$OCH$_2$—, —CH$_2$SCH$_2$— or C$_{1-6}$alkylene group; X$_3$ is an oxygen or sulphur atom; A$_3$ is phenyl, substituted phenyl, furyl, aminothiazolyl or aminothiadiazolyl in which the amino group is optionally protected; and A$_4$ is hydrogen, C$_{1-6}$alkyl, C$_{3-8}$cycloalkyl, C$_{3-8}$cycloalkyl(C$_{1-6}$)alkyl, C$_{1-6}$alkoxycarbonyl(C$_{1-6}$)alkyl, C$_{2-6}$alkenyl, carboxyC$_{1-6}$alkyl, C$_{2-6}$alkynyl, aryl or C$_{1-6}$alkyl substituted by up to three aryl groups; wherein the optional substituent is R$_4$ as defined below;

CO$_2$R$^3$ is a carboxy group, a carboxylate anion, or a readily removable carboxy protecting group of formula (i), (ii), (iii), (iv) or (v):

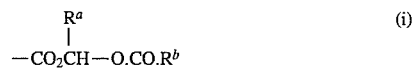

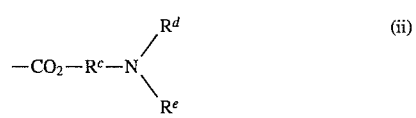

-continued

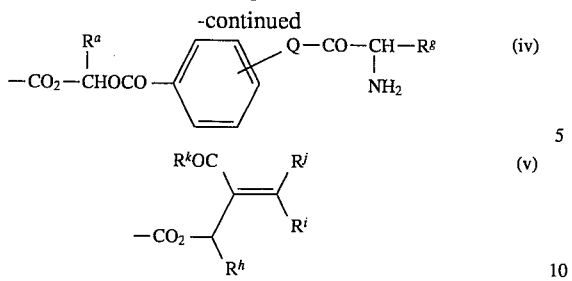

wherein $R^a$ is hydrogen, $C_{1-6}$alkyl, $C_{3-7}$cycloalkyl, methyl, or phenyl, $R^b$ is $C_{1-6}$alkyl, $C_{1-6}$alkoxy, phenyl, benzyl, $C_{3-7}$cycloalkyl, $C_{3-7}$cycloalkyloxy, $C_{1-6}$alkyl $(C_{3-7})$ cycloalkyl, 1-amino $(C_{1-6})$ alkyl, or 1-$(C_{1-6}$alkyl)amino $(C_{1-6})$alkyl; or $R^a$ and $R^b$ together form a 1,2-phenylene group optionally substituted by one or two methoxy groups; $R^c$ represents $C_{1-6}$alkylene optionally substituted with a methyl or ethyl group; $R^d$, $R^e$ and $R^f$ independently represent $C_{1-6}$alkyl; $R^g$ represents hydrogen or phenyl optionally substituted by up to three of halogen; $C_{1-6}$alkyl, or $C_{1-6}$alkoxy; Q is oxygen or NH; $R^h$ is hydrogen or $C_{1-6}$alkyl, $R^i$ is hydrogen, $C_{1-6}$alkyl optionally substituted by halogen, $C_{2-6}$alkenyl, $(C_{1-6}$alkoxy)carbonyl, aryl or heteroaryl; or $R^h$ and $R^i$ together form $C_{1-6}$alkylene; $R^j$ represents hydrogen, $C_{1-6}$alkyl or $(C_{1-6}$alkoxy) carbonyl; and $R^k$ represents $C_{1-8}$alkyl or $C_{1-8}$alkoxy, $C_{1-6}$alkoxy$(C_{1-6})$alkoxy or aryl;

$R^4$ represents hydrogen or up to four of $C_{1-6}$alkyl, $C_{2-6}$alkenyl, $C_{2-6}$alkynyl, $C_{1-6}$alkoxy, hydroxy, halogen, amino, $C_{1-6}$alkylamino, acylamino, $(C_{1-6}$dialkyl)amino, $CO_2R$, $CONR_2$, $SO_2NR_2$, wherein R is hydrogen or $C_{1-6}$alkyl, aryl or heterocyclyl, which may be the same or different and wherein any $R^4$ alkyl substituent is optionally substituted by any other $R^4$ substituent;

X is S, SO, or $SO_2$;

Y is S; and m is 1 or 2;

wherein "aryl" is phenyl or naphthyl, each optionally substituted with up to five of halogen, mercapto, $C_{1-6}$alkyl, phenyl, $C_{1-6}$alkoxy, hydroxy $(C_{1-6})$ alkyl, mercapto $(C_{1-6})$ alkyl, halo$(C_{1-6})$alkyl, hydroxy, amino, nitro, carboxy, $C_{1-6}$alkylcarbonyloxy, $C_{1-6}$alkoxycarbonyl, formyl, or $C_{1-6}$alkylcarbonyl groups; "heterocyclyl" and "heterocyclic" is an aromatic or non-aromatic, single or fused ring containing from 4 to 7 ring atoms which atoms may be up to four of oxygen, nitrogen or sulphur, which rings may be substituted by up to three of halogen, $C_{1-6}$alkyl, $C_{1-6}$alkoxy, halo $(C_{1-6})$ alkyl, hydroxy, carboxy, carboxy salts, $C_{1-6}$alkoxycarbonyl, $C_{1-6}$alkoxycarbonyl $(C_{1-6})$ alkyl, aryl, or oxo; and "heteroaryl" is an aromatic heterocyclic ring.

2. A compound as claimed in claim 1 having the formula (Ia):

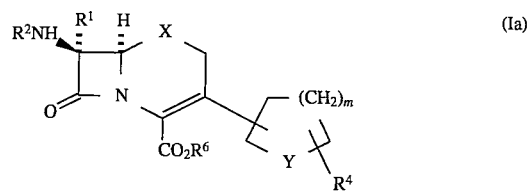

wherein $R^1$, $R^2$, $R^4$, m and X are as defined with respect to formula (I) in claim 1 and the group $CO_2R^6$ is $CO_2R^3$ where $CO_2R^3$ is a carboxy group or a carboxylate anion, or a pharmaceutically acceptable salt or in vivo hydrolysable ester thereof.

3. A compound as claimed in claim 2 wherein $A_3$ is 2-aminothiazol-4-yl and $A_4$ is hydrogen or methyl.

4. A compound as claimed in claim 1 wherein m is 1.

5. A compound as claimed in claim 1 which is pivaloyloxymethyl (6R,7R)-7-[2-(2-aminothiazol-4-yl)-2-(Z)-methoxyiminoacetamido]-3-[(RS)-tetrahydrothien-2-yl] ceph-3-em-4-carboxylate.

6. A pharmaceutical composition as claimed in claim 1 further comprising a β-lactamase inhibitor.

7. A method of treating bacterial infections in humans and animals which comprises administering a therapeutically effective amount of a compound of formula (Ia) or a pharmaceutically acceptable salt or in vivo hydrolysable ester thereof, as defined in claim 1, to a human or animal.

8. A pharmaceutical composition as claimed in claim 7 further comprising a β-lactamase inhibitor.

9. A method of treating bacterial infections in humans and animals which comprises administering a therapeutically effective amount of a compound of formula (Ia) or a pharmaceutically acceptable salt or in vivo hydrolysable ester there of as defined in claim 2, to a human or animal.

* * * * *